United States Patent [19]

Salomon

[11] 4,164,815
[45] Aug. 21, 1979

[54] DEVICE FOR MEASURING A HUMAN FOOT

[75] Inventor: Georges P. J. Salomon, Annecy, France

[73] Assignee: Establissements Francois Salomon et Fils, Annecy, France

[21] Appl. No.: 793,935

[22] Filed: May 5, 1977

[30] Foreign Application Priority Data

May 6, 1976 [FR] France .................. 76 13596

[51] Int. Cl.² .................................. A43D 1/02
[52] U.S. Cl. .............................. 33/3 A; 33/3 C; 33/174 D
[58] Field of Search ............... 33/3 R, 3 A, 3 B, 3 C, 33/6, 174 D

[56] References Cited

U.S. PATENT DOCUMENTS

| | | | |
|---|---|---|---|
| 33,307 | 9/1861 | Lane | 33/3 B |
| 263,971 | 9/1882 | Schaefer | 33/3 B |
| 1,030,763 | 6/1912 | Ashton | 33/3 A |
| 1,670,693 | 5/1928 | Sidwell | 33/3 C |

FOREIGN PATENT DOCUMENTS

| | | | |
|---|---|---|---|
| 42707 | 3/1888 | Fed. Rep. of Germany | 33/3 B |
| 165158 | 11/1905 | Fed. Rep. of Germany | 33/3 B |
| 219287 | 2/1910 | Fed. Rep. of Germany | 33/3 C |
| 285273 | 6/1915 | Fed. Rep. of Germany | 33/3 B |

*Primary Examiner*—Richard R. Stearns
*Attorney, Agent, or Firm*—Pollock, Vande Sande & Priddy

[57] ABSTRACT

A device for measuring the human foot comprises: (a) at least one element consisting of a supporting surface for the bottom of the heel and a stop for the back of the heel; and (b) a graduated tape connected to the above element and surrounding the foot in an area passing through the rear end of the heel-bone and through the joint between the ankle bone and the scaphoid bone, the free end of the tape sliding in a passage and emerging from the device so that it can be grasped. This measuring device makes it possible to determine the type of boot best suited to the foot measured.

12 Claims, 19 Drawing Figures

DEVICE FOR MEASURING A HUMAN FOOT

The present invention relates to a device for obtaining information regarding at least one dimension of the human foot, the information being used to select a boot of the correct size.

It is generally known that the size of a person's foot is determined by measuring the distance between the back of the heel and the toe which projects the farthest, the size thus determined then making it possible to select a suitable boot from a predetermined range.

However, in the case of footwear in which one fundamental characteristic is satisfactory foot retention, for example boots for skiing, mountain-climbing, and ices-kating, there are disadvantages in using length as the parameter representing the dimensions of the foot.

Figure 1:
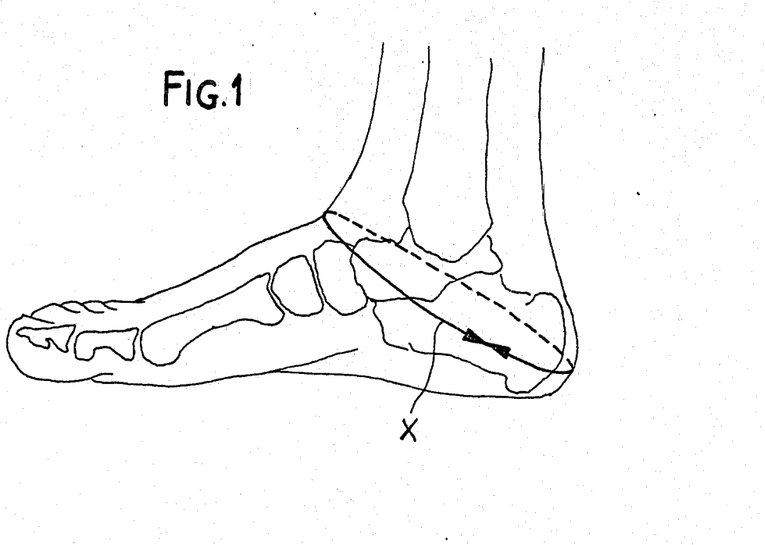
FIGS. 1 and 2 are diagrams of a foot defining the SHP and the width of the foot.

For this reason, and as set forth in application Ser. No. 793,938, filed May 5, 1977 under the title "Method for fitting boots and a correlation table", it is proposed to use, as a representative parameter in selecting a boot, not the length of the foot, but another dimension of the foot taken in a plane passing substantially through the rear end of the heel-bone and through the area of articulation between the ankle-bone and the scaphoid-bone, this dimension being referred to hereinafter, for the sake of clarity, as the "short heel perimeter" or "SHP." In other words, the SHP is the length of the perimeter, as measured on a foot at rest, of the figure defined by an imaginary plane passing through the rear end of the heel-bone and through the joint between the ankle-bone and the scaphoid-bone, i.e., the connecting line between the leg and the foot. FIG. 1 of the drawings attached hereto shows the location of the SHP (line X) on the foot, the latter being indicated with a fine line.

The present invention therefore relates to a device for measuring this SHP dimension, and is characterized in that it comprises at least one support for the heel of the foot and at least one measuring element connected to the support and adapted to pass around the foot in the vicinity of the SHP, the measuring element being adapted to provide the information relating to the SHP dimension.

The support may, with advantage, be in the form of a seating surface for the underside of the heel, with at least one stop for the back of the heel, the stop forming a specific angle with the seating surface. The foot may therefore be placed in a specific position in which the leg forms a constant angle with the sole of the foot, as soon as the stop and the seating surface are connected rigidly together, in accordance with the invention. Preferably, and again in accordance with the invention, the stop and the seating surface are at right angles, and the stop may be either a plane or a dihedron in which the back of the heel may easily be placed.

The measuring element may, with advantage, be in the form of a flexible strap (such as a tape, cord, wire, etc.), one end of which is secured to the support, more particularly to the stop in the vicinity of the heel, while the other end is free and is used to fit the strap to the foot. The free end of the strap may, with advantage, be accommodated slidingly in a passage within the thickness of the stop. The strap also has reference markings in the form of graduations which move, when the strap slides in its passage, in front of an indicator fitted to the support. It is thus possible to read off the measured length of the SHP.

Conversely, the strap may carry the indicator, the latter passing in front of system of markings arranged on the support and constituting a table of boot sizes.

Figure 2:
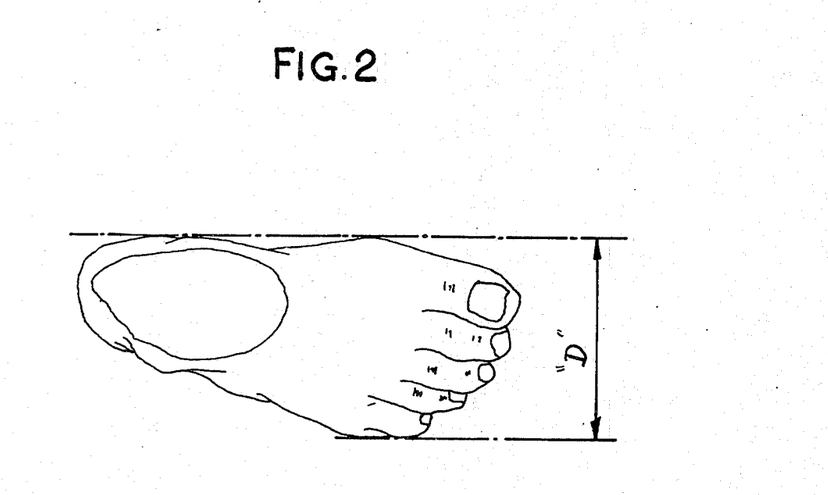

According to another aspect of the invention, the measurement of the SHP is complemented by measuring another dimension of the foot, namely the width thereof, i.e., the distance between parallels, one of which passes through the two bony projections on the inside of the foot, while the other passes through the bony projection on the outside of the foot, as shown at "D" in FIG. 2.

According to still another aspect of the invention, therefore, the device is also equipped with means for measuring the width of the foot at the same time as it is measuring the SHP. In the case of feet which have the same SHP, this makes it possible to take into account variations in width from one foot to another, due to the condition of, inter alia, the plantar arch. This means for measuring the width of the foot consists, according to the invention, of a first supporting element for the inside of the foot and a second supporting element for the outside of the foot, the two elements being parallel one with the other, and at least one of them being movable in relation to the other. The means for measuring the width of the foot is also equipped with a system of markings and an index, so that the result of the measurement can be read off directly.

A description will now be given of several embodiments of the invention, in conjunction with the drawings attached hereto, wherein.

The two first embodiments of the invention make it possible to measure the SHP (FIGS. 3 to 8). The four following embodiments (FIGS. 9 to 19) make it possible to measure the SHP and the width of the foot in a single operation.

With these two measurements, the size of the boot may be selected according to the SHP measurement, but within this size there can be a plurality of widths (wide, medium and narrow, for example). It would also be possible to use a completely different principle, based upon the SHP and the width of the foot.

Figure 3:
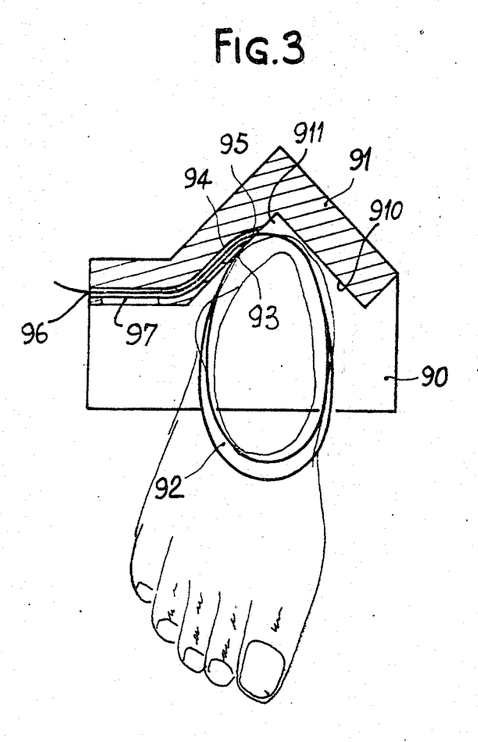
FIGS. 3, 4 and 5 illustrate a first embodiment of the device according to the invention, FIG. 4 being a front elevation, FIG. 3 being a section along line AA in FIG. 4, and FIG. 5 being a side elevation.
Figure 4:
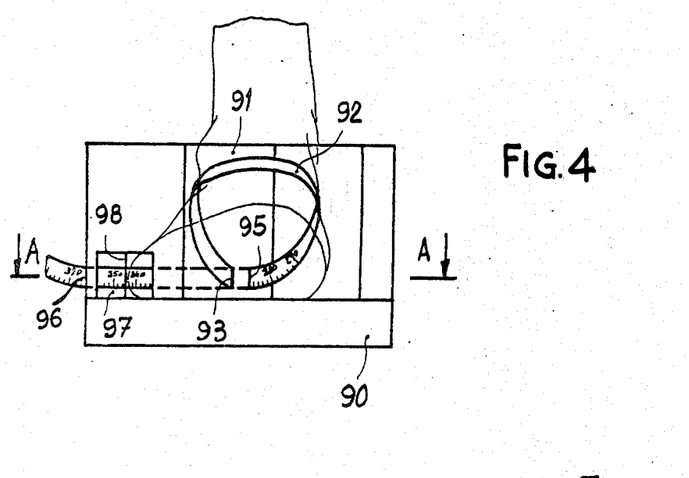
Figure 5:
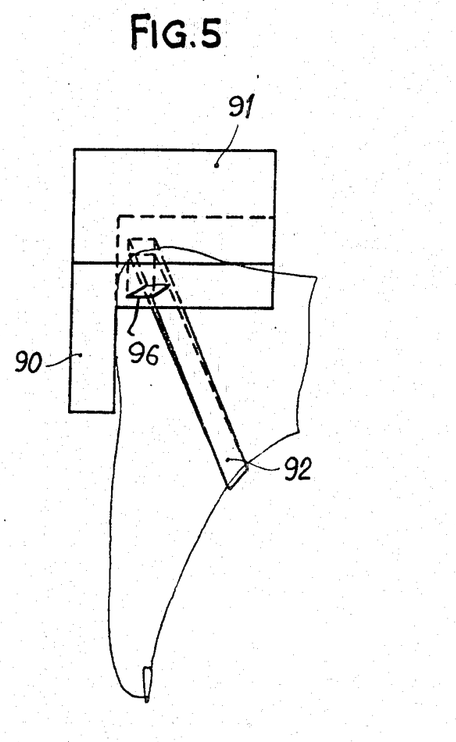

FIGS. 3, 4 and 5 illustrate a first embodiment of the invention, in which only the SHP is measured. In this case, the heel of the foot to be measured is placed in a reference support consisting of a seating surface 90 for the bottom of the heel and a V-shaped, or dihedral, stop designed to accommodate the back of the heel; the internal surfaces 910 and 911 of the V are substantially perpendicular to the base. Seating surface 90 and stop 91 may be in one piece or in two pieces rigidly connected one to the other. One end of a flexible tape 92 is secured to the support, more particularly to the stop, at a point 93 in the vicinity of the heel, the attachment being made by any suitable known means. Tape 92 forms a loop designed to surround the foot in the SHP area, and it enters slidingly into a passage or housing 94 in the support, more particularly in the stop, where the heel is going to rest; in the example illustrated, inlet 95 to passage 94 is close to point 93 where the tape is secured to the stop.

Passage 94 opens out at a point 96, where tape 92 emerges. Located near the outlet 96 is a window 97 in stop 91 designed to allow a portion of the tape to be seen. This window may be fitted with a transparent plastic cover, or with a magnifying glass, and with an indicator 98 (a wire, for example), the graduations or numbers marked on the tape passing in front of the indicator. In order to measure the SHP, the foot is placed in the loop formed by tape 92 and is caused to bear against elements 90,91. The operator tightens tape 92 by its free end, which emerges from outlet 94, and reads off the SHP measurement on the tape at indicator 98. Care must be taken to assure that the tape is long enough for its free end to emerge from the device, regardless of the length of the SHP to be measured. The graduations on the tape must, of course, allow for the distance between points 93 and 95, and for the length of passage 94, so that the exact length of the SHP measured can be read off directly.

The tape may be graduated in millimeters (as in FIG. 4), or it may indicate directly the correct size of boot for the foot thus measured.

The device according to FIGS. 3 to 5 is very light and easily carried, and the measurement may be carried out very quickly. However, since the stop is not very high, a certain number of precautions must be taken in order to position the leg correctly in relation to the sole of the foot, since in this embodiment the ankle joint remains free. Therefore, depending upon the angle formed between the leg and the sole of the foot, and upon the position of the toes, the big-toe extensor muscle projects to a greater or lesser degree, and this may produce variations in the SHP measurement. These variations may influence the choice of the boot and therefore the wearer's comfort and, if they are to be avoided, every effort will be made to assure that, while the measurements are being taken, the angle between the leg and the sole of the foot is constant, and that the toes are in a specific position. This will assure that the measurement is not falsified by the state of contraction of the big-toe extensor muscle.

Figures 6, 8:
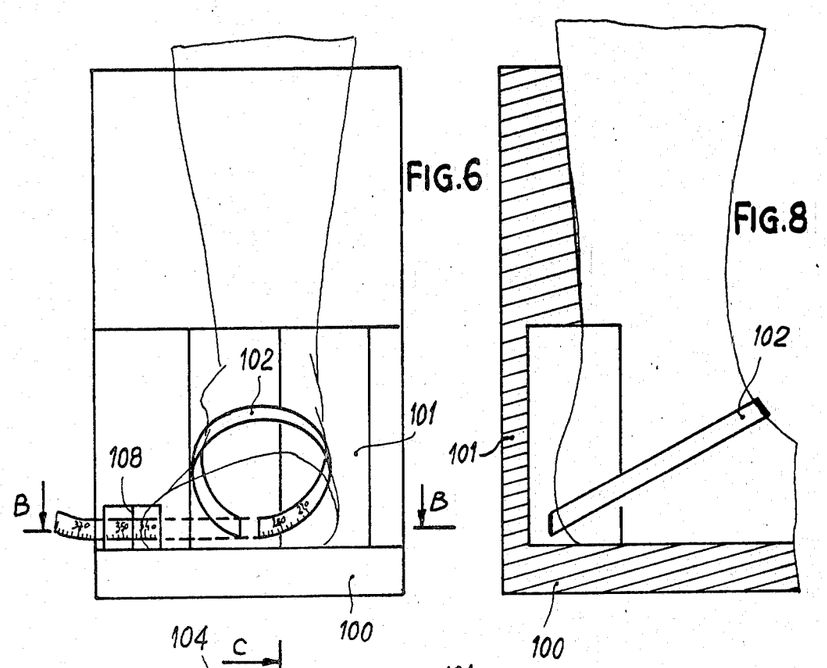
FIGS. 6, 7 and 8 illustrate a second embodiment of the device, FIG. 6 being a front elevation, FIG. 7 being a section along line BB in FIG. 6, and FIG. 8 being a section along line CC in FIG. 7.
Figure 7:
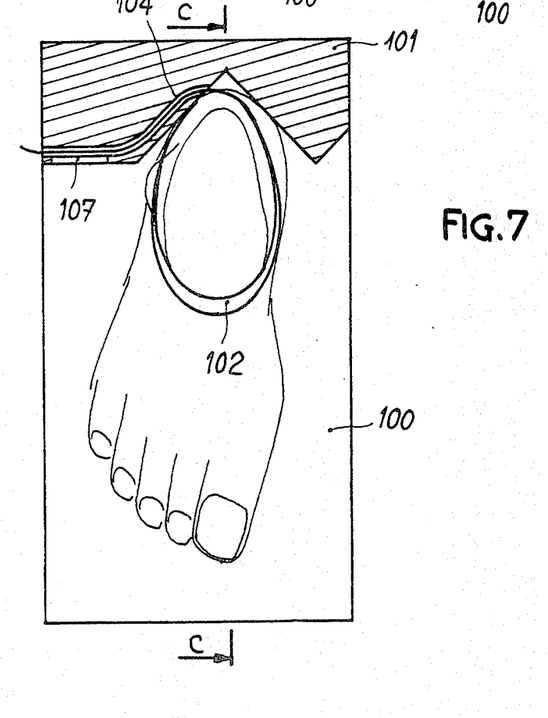

Illustrated in FIGS. 6, 7 and 8 is a variant of the device which establishes these relationship in a simple manner by increasing the height of the stop behind the leg and extending the seating surface under the toes.

The concept of this second embodiment is similar to that of the first, but seating surface 100 has been extended under the entire sole of the foot, and stop 101, for the back of the heel, has been extended almost to the bottom of the calf. The lower part of this stop 101 has a V-shaped or dihedral recess as in the previous embodiment, for the purpose of positioning the heel laterally. As in the preceding example, a graduated tape 102 secured to stop 101 surrounds the foot and enters a passage 104 in the stop, in which it slides in front of a window fitted with an indicator 108.

Figure 9:
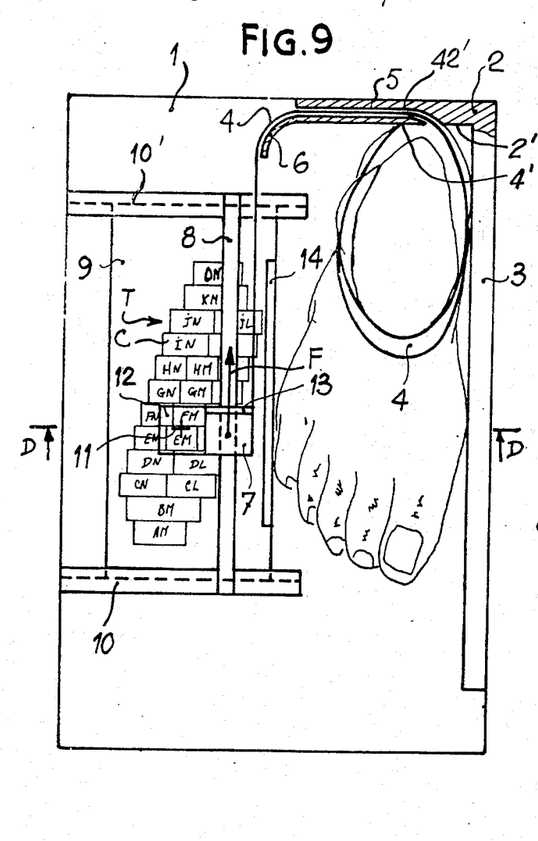
FIGS. 9, 10 and 11 illustrate a third embodiment of the invention, FIG. 9 being a plan view of the device from above, FIG. 10 being a section along line DD in FIG. 9, and FIG. 11 being a side elevation.
Figure 10:
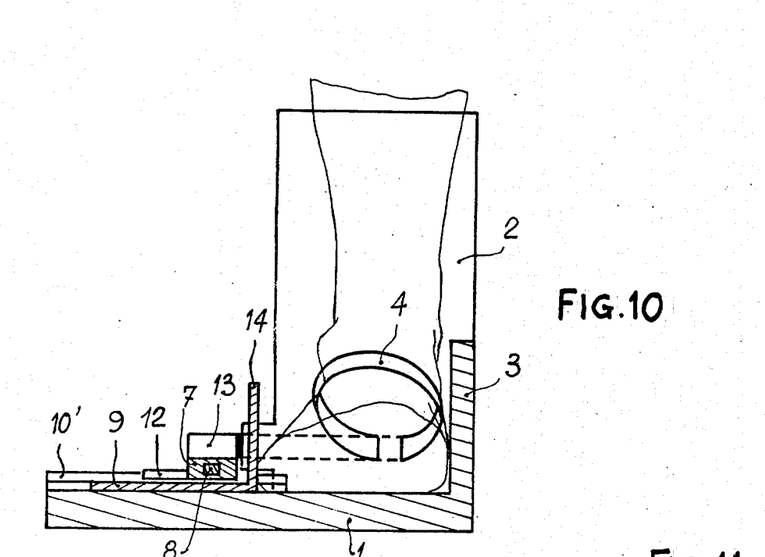
Figure 11:
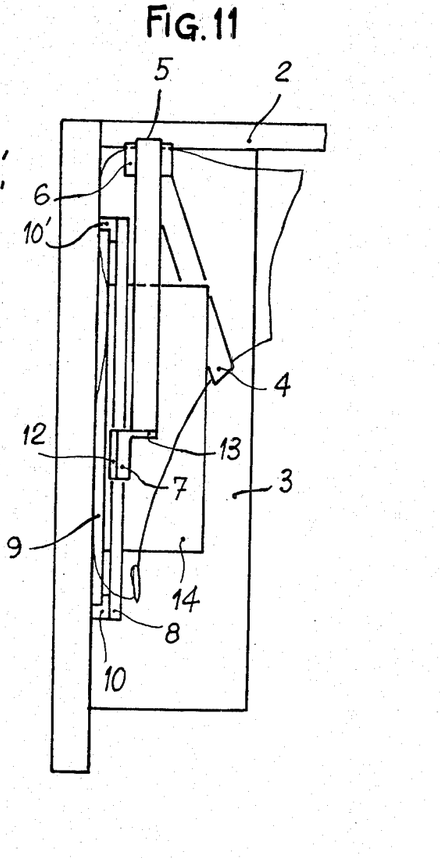

FIGS. 9, 10 and 11 illustrate a third embodiment, making it possible to measure the SHP and the width of the foot in a single operation. In this case, the device consists of:

1. a seating surface 1 supporting the sole of the foot;
2. a stop 2 for the back of the heel which, in the example illustrated, has a flat inside wall 2'; this heel stop preferably extends upwardly (to the bottom of the calf) so that when the leg bears against it, the angle between the leg and the sole of the foot is accurately determined, as in the second embodiment; and
3. a support element, for example a plate 3 integral with the seating surface and at right angles thereto. The bony projections on the inside edge of the foot bear against this plate.

The foot is thus held correctly in place within a three-dimensional reference system.

A flexible tape 4 is secured at 4' to the inside wall of heel stop 2 in the contact area thereof; the tape forms a loop surrounding the foot in the SHP area and then enters a passage 5 in the stop. This tape passes over a deflector 6 (for example a curved guide as in FIG. 9 or a pulley) and is secured to a cursor 7 running on a slide or guide 8 parallel with support plate 3, the ends of the guide being attached to slides 10,10' which are integral with seating surface 1 and extend at right angles to plate 3.

Cursor 7 comprises a transparent part 12, made of glass or plexiglass, for example, upon which is engraved an indicator 11, for example a cross; the cursor also has a projecting part 13 whereby the operator can move it along slide 8.

A mobile guide 9 runs in slides 10,10' at right angles to support plate 3. This guide has a vertical member 14 designed to bear against the bony projection on the outside edge of the foot, the vertical member also being used to move the guide. Guide 9 may be fitted with an axis parallel with support plate 3, graduated as a function of the SHP, and with a vertical axis graduated as a function of foot widths; this arrangement, in conjunction with an indicator 11 and a cartesian reference system, indicates the width of the foot (along the abscissae) and the SHP (along the ordinates).

Preferably, however, and as shown in FIG. 9, guide 9 is designed to indicate directly the model of boot suitable for the foot measured. As may be seen in the drawing, guide 9 is graduated in three boot widths for medium SHP's, two boot widths for small and large SHP's, and a single boot width for extreme SHP's.

In order to measure a foot, cursor 7 is moved in the direction of arrow F in order to loosen the loop in tape 4; the foot is then introduced into the loop and is positioned in relation to the three reference planes 1,2,3. Cursor 7 is then moved in the direction opposite to that of arrow F to tighten tape 4 around the foot.

Part 14 of guide 9 is then applied to the bony projection on the outside edge of the foot, after which the two measurements may be read off the apparatus.

In the example illustrated in FIG. 9, guide 9 has reference markings in the form of a table T with 24 boxes C each containing two letters. The first letter indicates SHP sizes (increasing from A to O), while the second letter indicates the widths available in each SHP size. In the example illustrated, three widths are available, namely average (M), wide (L), and narrow (N). It is thus possible with this device to determine immediately the model of boot best suited to the user, based upon his SHP and foot width.

It will be noted that this apparatus is highly flexible in use, since one, two or three widths can be provided for a given SHP. Obviously the number of widths for a given SHP may vary, depending upon what the customers want. Furthermore, it is quite easy to alter the number of widths for a given SHP, or to alter the SHP and foot-widths ranges for a given boot, merely by substituting a different guide 9, or by using any other sizing system based upon measuring the SHP and foot width.

As may be gathered from FIG. 9, the type of boot suitable for a particular foot will be given by box C in front of which will be located indicator 11 carried by cursor 7. In the case illustrated in FIG. 9, therefore, EM will be the correct boot for the foot measured, i.e., a boot for an SHP length E and a medium width.

Where guide 9 is graduated in millimeters (not shown) along two axes of cartesian coordinates, the operator reads the SHP on one of the axes (the one with the ordinates) and the foot width on the other axis (the one with the abscissae). He may then select the correct boot from a chart which correlates these dimensions with a boot model. It will be understood that, instead of being permanently secured at 4' to stop 2, tape 4 could be secured detachably at that point, in order to facilitate the positioning of the foot.

Figure 12:
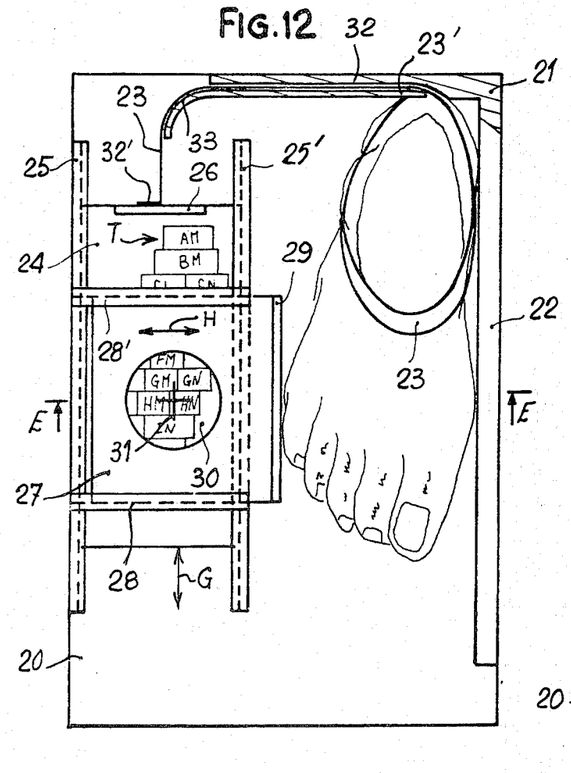
FIGS. 12, 13 and 14 illustrate a fourth embodiment, FIG. 12 being a plan view of the measuring device, FIG. 13 being a section along line EE in FIG. 12, and FIG. 14 being a side elevation.
Figure 13:
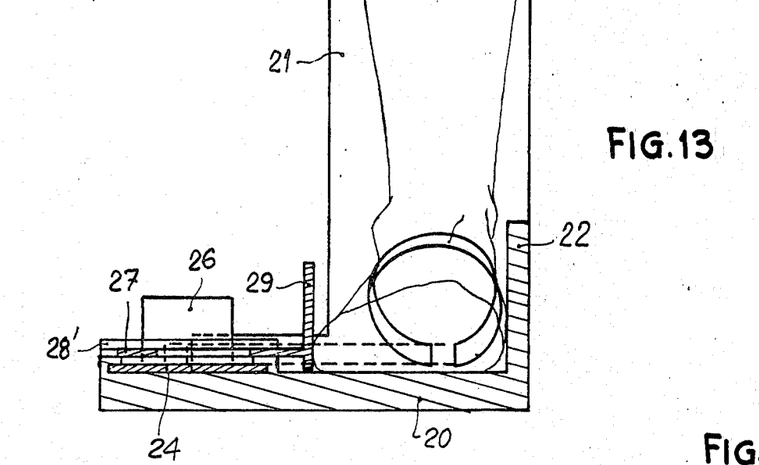
Figure 14:
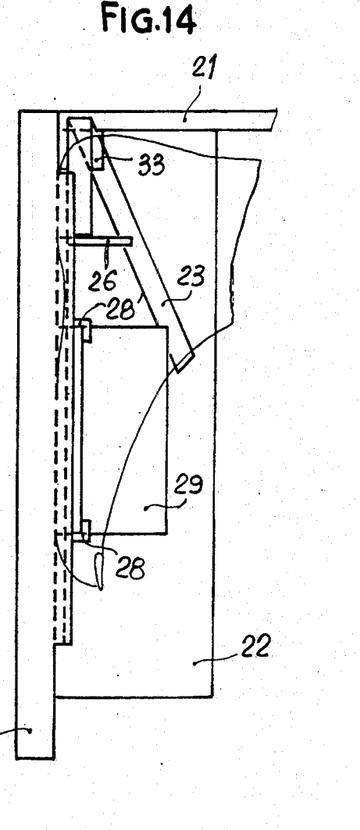

FIGS. 12, 13 and 14 illustrate a fourth embodiment of the invention. In this case, the device according to the invention has the same reference supports for the foot: a supporting surface 20, a stop 21 for the back of the heel, and an element 22 against which the inside edge of the foot bears, each of these elements being perpendicular to the other two.

As before, the device has a tape 23 surrounding the foot to be measured. One end 23' of tape 23 is secured to stop 21, while the other end, after passing through a passage 32 in the stop, and over a deflector 33 provided by rounding off the stop, is secured at 32' to a movable plate 24 mounted in slides 25,25' secured to supporting surface 20 and parallel with support element 22. Plate 24 has a vertical projection 26 which allows it to be moved along slides 25,25' in the direction of double arrow G. This plate is graduated similarly to guide 9 mentioned above, i.e., it has a table T of boot sizes. It will be noted, however, that Table T in FIG. 12 is inverted as compared with that in FIG. 9, due to the fact that the plate is movably connected with tape 23.

A guide 27 runs between slides 28,28' parallel with stop 21 and is secured transversely to slides 25,25'. Guide 27 has a projection 29 by means of which it may be moved in the direction of double arrow H, and is designed to bear against the outside edge of the foot. The guide also has an aperture 30, with a glass or plastic cover, upon which is engraved an indicator, for example a cross 31 in the example illustrated. Aperture 30 thus makes it possible to see the table on plate 24 and to read off the reference for the correct type of boot, or the SHP and foot-width values, from the box in Table T selected by indicator 31. The measuring procedure is identical with that in the preceding embodiment.

Figure 15:
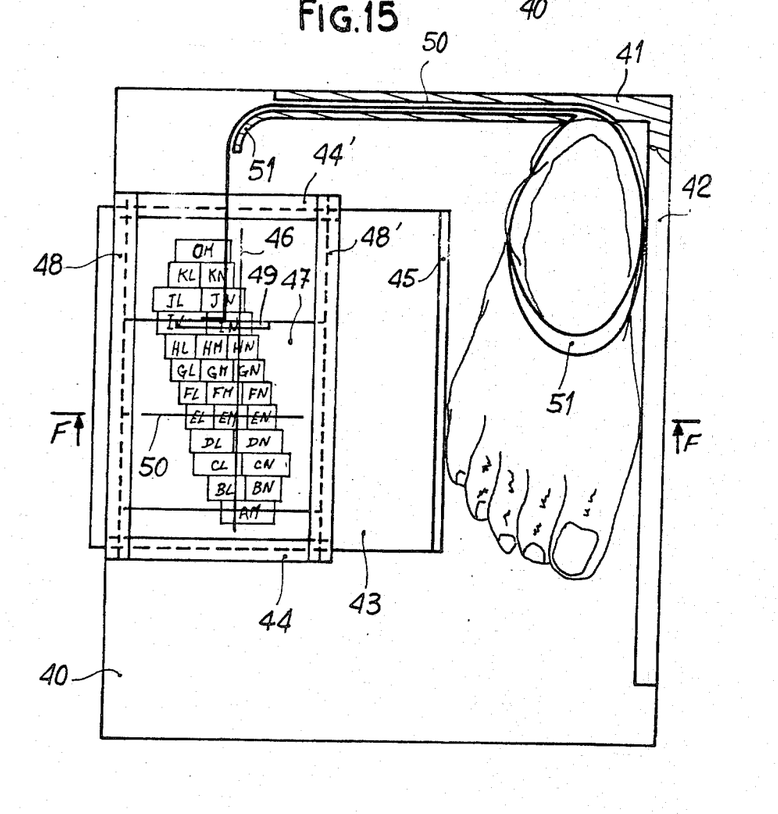
FIGS. 15 and 16 illustrate a fifth embodiment of the invention, FIG. 15 being a plan view of the apparatus, and FIG. 16 being a section along line FF in FIG. 15, and FIGS. 17, 18 and 19 illustrate a sixth embodiment of the invention, FIG. 17 being a plan view of the device, FIG. 18 being a section along line GG in FIG. 17, and FIG. 19 being a side elevation along line HH in FIG. 17.
Figure 16:
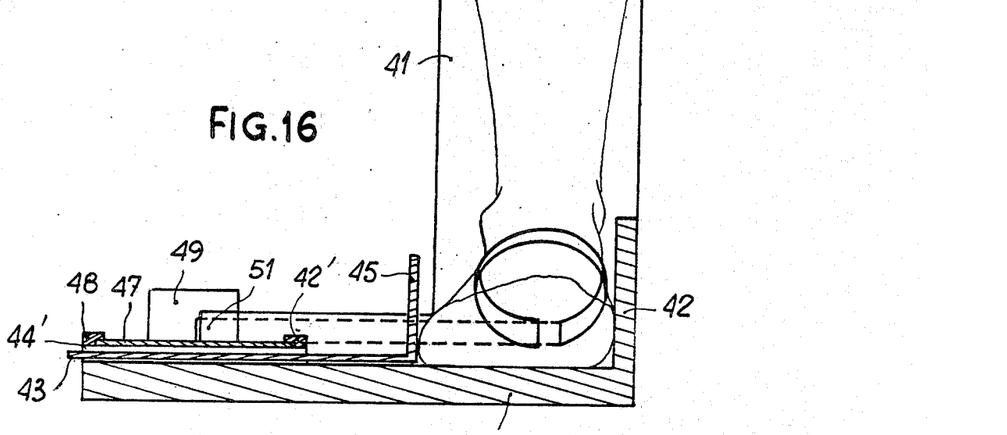

FIGS. 15 and 16 illustrate a fifth embodiment of the measuring device. As before, the apparatus consists of a support surface 40, a stop 41 for the back of the heel, and an element 42 bearing against the inside edge of the foot, these parts being integral and perpendicular two by two. In this design, the reference table is not engraved on a part moving transversely in relation to the foot (FIGS. 9 to 11) or longitudinally, but directly upon the supporting surface 40 which is stationary.

As may be seen in FIG. 15, a guide 43 runs in slides 44,44' which are parallel with stop 41 and are secured to supporting surface 40; the guide has a vertical part 45 by means of which it can be manipulated and which bears against the outside edge of the foot. The guide is preferably transparent, at least in the vicinity of an indicator 46 which is engraved thereon and which, in the example illustrated is in the form of a straight line parallel with element 42.

A plate 47 runs in slides 48,48' parallel with element 42 and secured to slides 44,44'; this plate has a vertical part 49 by means of which it may be manipulated, and an indicator 50, for example a straight line parallel with surface 40.

A tape 51, similar to tapes 4,23,92,102, surrounds the foot to be measured in the vicinity of the SHP, the tape being secured to plate 47 in such a manner that the displacement thereof indicates the SHP measurement.

Plate 47 is also made of a transparent material, so that the correct size reference for the foot can be read off surface 40.

The procedure for measuring the foot is similar to the procedures used in the preceding examples, the correct type of boot for the foot measured appearing at the intersection of indicators 46 and 50.

Figure 17:
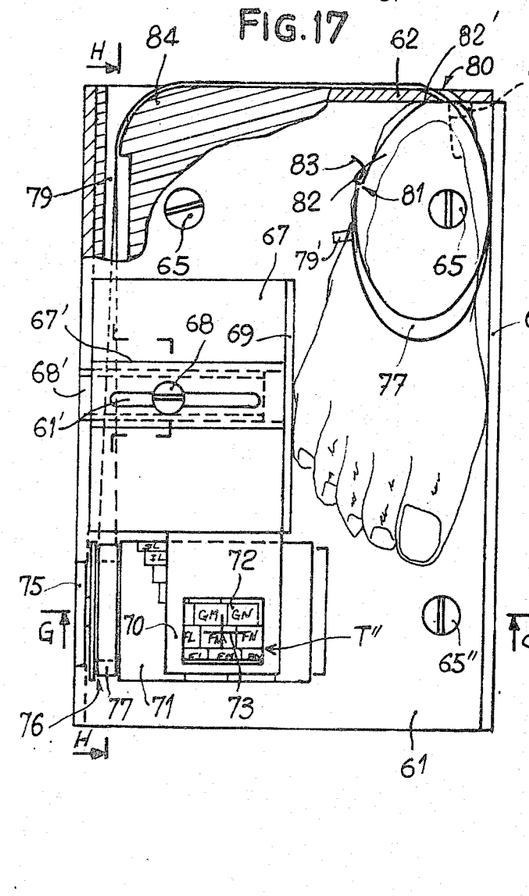
Figure 18:
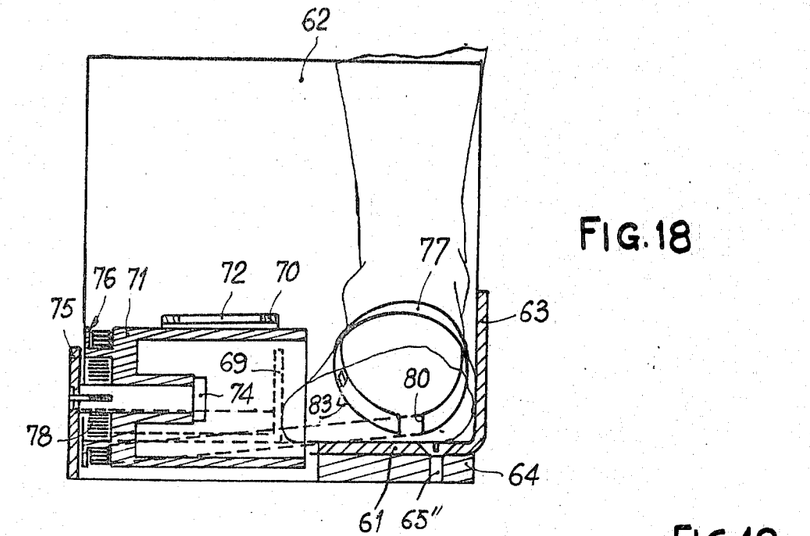
Figure 19:
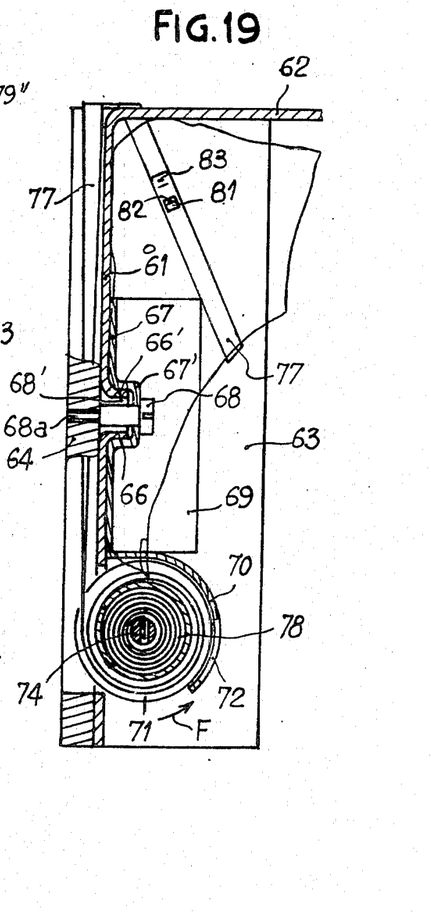

Another embodiment of the measuring device is shown in FIGS. 17, 18 and 19. In this case, reference table T" is arranged on a drum which is caused to rotate by a tape surrounding the foot to be measured.

As in the preceding embodiments, the device supports the foot in three reference planes, namely a surface 61 for the sole of the foot, a stop 62 for the back of the heel, and an element 63 bearing against the inside edge of the foot, these planes of reference being perpendicular two by two and being in the form of a bent sheet secured to a base 64 by means of screws 65", or any other suitable means.

As before, the three reference planes 61,62,63 constitute a reference system for the foot to be measured. Surface 61 is shaped to form guides 66,66' parallel with stop 62 and at right angles to surface 61. These guides, separated by a slot 68', form a slide for an element 67 sliding along an axis parallel with stop 62. Element 67 has a stamped rib 67', the upper surface of which has an oblong slot 61' traversed by a screw 68, the threaded part 68a of which is engaged in a hole drilled in base 64. Element 67 is thus obliged to move in the plane of surface 61 without lifting.

Element 67 has a part 69 which is bent at right angles, which runs parallel with supporting element 63, which is used to manipulate it, and which bears against the outside edge of the foot. Element 67 also has a curved cylindrical part 70 partly surrounding a drum 71 which will be described hereinafter. Part 70 has an opening 72 covered with glass or plastic upon which is engraved an indicator 73, for example a cross, by means of which the correct boot for the foot measured may be read off table T" as it passes under opening 72.

Drum 71 rotates freely upon an axis 74 which is stationary in relation to surface 61, being secured to a tongue 75 integral with surface 61 and parallel there-with. The axis is thus parallel both with surface 61 and with stop 62. An expansion at the free end of axis 74 holds the drum in the axial direction. The drum has a circular groove 76 in which a tape 77 is rolled, one end of the tape being secured to drum 71.

A spiral spring 78, one end of which is integral with axis 74 while the other end is integral with drum 71, urges the drum in the direction of arrow F in FIG. 19, thus rolling up tape 77. The tape runs in a passage 79 in base 64, passes over a curve 84 in base 64 which deflects it as it emerges from passage 79, slides behind heel-stop 62, and passes through a passage 80 in the stop, so that it can surround the foot in the vicinity of the SHP. In the example illustrated, the end of tape 77 has an eye 81 which can be secured detachably to a hook 82 secured at 82' to heel-stop 62. Beyond eye 81, tape 77 also has a protruding end 83 which allows the tape to be grasped and manipulated.

Attaching tape 77 detachably to hook 82 makes the device easier to handle, but it will be understood that a tape similar to those in the preceding embodiments may be used. Similarly, the devices previously described may have the hooking system shown in FIG. 17. In a manner similar to the preceding embodiments, the periphery of drum 71 carries a boot-size reference table which may be engraved on the drum or printed on a sheet fitted thereto.

When the tape is not in use, end 83 thereof is released from hook 82 and is rolled onto the drum by the action of helical spring 78. However, it must still be possible for end 83 of the tape to be grasped by the operator.

This may be achieved by means of a tape-stopping system arranged in passage 80, to prevent the tape from passing through the passage. For instance, as shown in dotted lines in FIG. 17, passage 80 may contain a section scarcely any larger than the tape and the tape may be made thicker at 79", near its end, than the constriction in passage 80. This makes it impossible for the tape to pass through the passage under the action of spring 78.

In order to measure the foot, the operator first of all unwinds enough tape to allow the foot to be placed in position conveniently. He then fits the tape around the foot in the vicinity of the SHP, securing free end 83 thereof to hook 82 by means of eye 81, the tape being held to the foot by the helical spring acting upon the tape.

The operator then moves guide 67 into contact with the foot, whereupon he may read off the correct boot model from the box in table T" facing indicator 73.

This apparatus has the advantage of eliminating handling errors, since the tension of the tape on the foot is always the same for a given SHP. The same result may be obtained in the preceding embodiments by subjecting parts 7,24 and 47 to the action of a spring.

It would also be possible to spring-load parts 9,27,67 and 47 to obtain more accurate foot-width measurements, but since this arrangement is within the capabilities of a technician, it will not be described in detail.

It will be noted that in the last four embodiments described, the stop for the back of the heel may be V-shaped, as in the two first embodiments.

Moreover, in the first two embodiments the graduations are on the tape and the indicator is on the apparatus, but the indicator may be on the tape and the graduations on the apparatus, without departing from the scope of the invention.

It is obvious that the devices described above will preferably stand on the floor if the person whose foot is to be measured is standing up. If the person is sitting down, the device should be placed upon a sloping surface.

It should be noted that the measuring devices described above are designed mainly for measuring the right foot, and that a symmetrical device would naturally make it possible to measure the left foot. Furthermore, the edge of the foot used as the reference is the inside edge, although it would also have been possible to use the outside edge of the foot for this purpose.

What is claimed is:

1. A device for obtaining information regarding at least one dimension of a human foot, more particularly for the purpose of selecting a boot suitable for said foot, comprising
    (a) a rigid trihedral support structure having a substantially horizontal and two substantially vertical planes forming reference faces for placement of the foot to be measured in a fixed position, said reference faces defining between them an interior face of said structure;
    (b) a passage within at least one of said faces of said structure adjacent to the position of the heel of said foot when in position to be measured, said passage opening in said interior space of said structure; and
    (c) means for connecting at least one measuring element to said structure by one of its ends adjacent the intersection of said three planes;
    (d) the opening of said passage within the interior space of said structure being located adjacent the point of connection of said measuring element to said structure and the other end of said measuring element being free for sliding movement within said passage.
2. A device according to claim 1, wherein the planes of said trihedral support structure are perpendicular each to the others.
3. A device according to claim 1, wherein said passage and said means for connecting said measuring element are located on one of said vertical planes.
4. A device according to claim 1, including a fixed measurement indicator located on a portion of said structure on a level with said passage, said measuring element having graduated markings thereon.
5. A device according to claim 1, wherein said planes of said structure are so arranged as to compel a standard positioning of the foot to be measured, said horizontal plane providing the support for placement of said foot, a first one of said vertical planes providing support and orientation for one side of said foot, and the second of said vertical planes providing a stop at the back of the heel limiting longitudinal displacement of said foot.
6. A device according to claim 5, wherein said horizontal face of said structure comprises a guide means extending perpendicularly to said first vertical plane, said guide means having thereon a movable slide with a side extending parallel to said first vertical plane and adapted to abut against the other side of said foot, means for showing the width of said foot as repesented by the distance between said first vertical plane and said movable slide being provided on said horizontal face of said structure.
7. A device according to claim 6, wherein said free end of said measuring element is attached to a cursor provided with an index moving on a sliding element attached to said horizontal face and extending parallel to the latter and to said first vertical face, while said movable slide is provided with markings whereby the measurement results can be read.

8. A device according to claim 6, wherein said free end of said measuring element is attached to a movable plate mounted in slides secured to said horizontal plane for displacement in a direction parallel to both said horizontal face and to said first vertical face, said movable plate having thereon reference markings grouped in tables, while said movable slide for measuring the width of said foot comprises an indicator and is slidably and transversely mounted in slides attached to said slides in which said movable plate is mounted.

9. A device according to claim 6, wherein the free end of said measuring element is attached to a movable plate mounted in slides for movement in a direction parallel to both said horizontal face and to said first vertical face, said plate comprising a first indicator consisting of a line transverse to said first vertical plane, while said slide movable in a direction transverse to that of said movable plate comprises an indicator consisting of a line parallel to said first vertical plane, said horizontal face having thereon markings grouped in tables and visible through said movable plate and slide, the intersection of the indicators carried by the latter showing the measurement results.

10. A device according to claim 6, comprising a rotatable drum connected to said free end of said measuring element for regulating the tension thereof, said drum having a spiral spring for maintaining it in a state of permanent tension relative to said device, said drum having thereon reference markings cooperating with a facing indicator.

11. A device according to claim 10, wherein said indicator is carried by a movable slide for cooperating with said markings carried by said drum.

12. A device according to claim 6, wherein said movable slide for measuring the width of said foot is slidingly mounted on a supporting slide extending perpendicularly to said first vertical face.

* * * * *